United States Patent [19]

Teoh et al.

[11] Patent Number: 5,368,577
[45] Date of Patent: Nov. 29, 1994

[54] NEEDLE STICK PREVENTION DEVICE

[75] Inventors: Phillip Teoh; Clifford Teoh, both of Daly City, Calif.

[73] Assignee: Biocon International Corporation, Daly City, Calif.

[21] Appl. No.: 66,791

[22] Filed: May 24, 1993

[51] Int. Cl.⁵ .................. A61M 5/32; A61M 5/50
[52] U.S. Cl. ............................ 604/198; 604/110
[58] Field of Search ..................... 604/192–198, 604/110, 263

[56] References Cited

U.S. PATENT DOCUMENTS

| | | | |
|---|---|---|---|
| 4,738,663 | 4/1988 | Bogan | 604/198 |
| 4,781,684 | 11/1988 | Trenner | 604/110 |
| 4,795,432 | 1/1989 | Karczmer | 604/110 |
| 4,846,805 | 7/1989 | Sitar | 604/165 |
| 4,850,994 | 7/1989 | Zerbst et al. | 604/198 |
| 4,874,384 | 10/1989 | Nunez | 604/198 |
| 5,013,301 | 5/1991 | Marotta, Jr. et al. | 604/197 |
| 5,116,319 | 5/1992 | Van den Haak | 604/110 |
| 5,226,894 | 7/1993 | Haber et al. | 604/198 |
| 5,269,761 | 12/1993 | Strehrenberger et al. | 604/110 |
| 5,279,582 | 1/1994 | Davison et al. | 604/198 |

*Primary Examiner*—John D. Yasko
*Assistant Examiner*—Adam J. Cermak
*Attorney, Agent, or Firm*—Townsend and Townsend Khourie and Crew

[57] ABSTRACT

A needle stick prevention device for a syringe. The syringe includes a barrel, a hub having a needle attached thereto, and a shoulder extending between the hub and barrel. A sleeve is slidably coupled to the syringe between a retracted position, in which the needle extends through an aperture in the top of the sleeve, and an extended position, in which the needle is housed within the sleeve. The sleeve has first and second slots cut into the sidewall. A retaining clip has first and second legs which are positioned in the first and second slots, respectively. The first and second legs exert a compressive force on the syringe barrel when the sleeve is in the retracted position to hold the sleeve in the retracted position. An upper stop extends radially outward from the hub. The first and second legs are biased inwardly between the upper stop and the shoulder when the sleeve is in the extended position to hold the sleeve in the extended position.

10 Claims, 3 Drawing Sheets

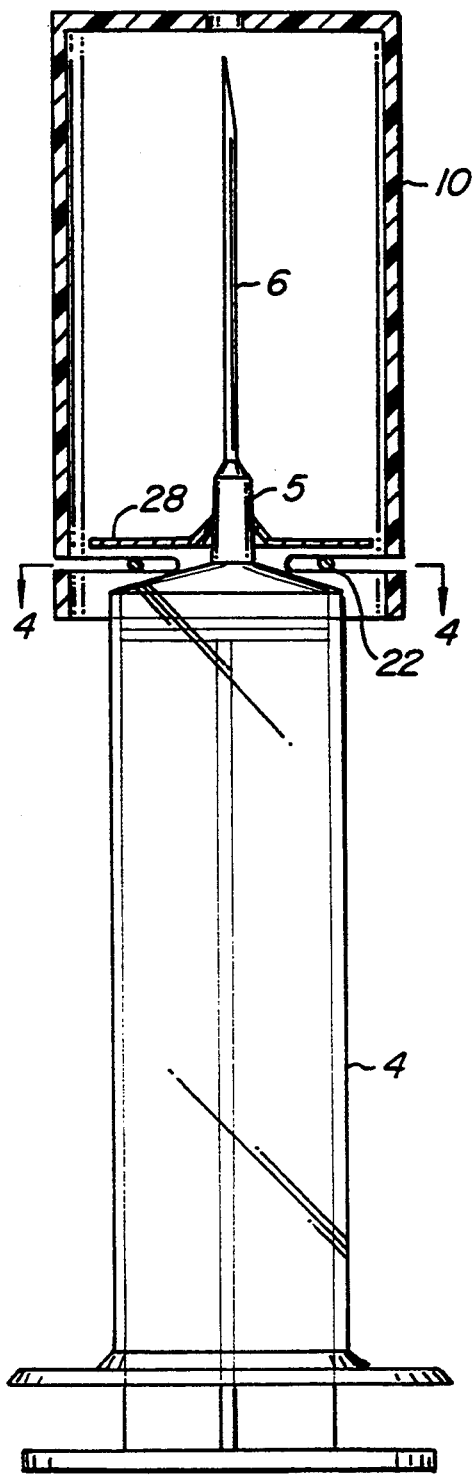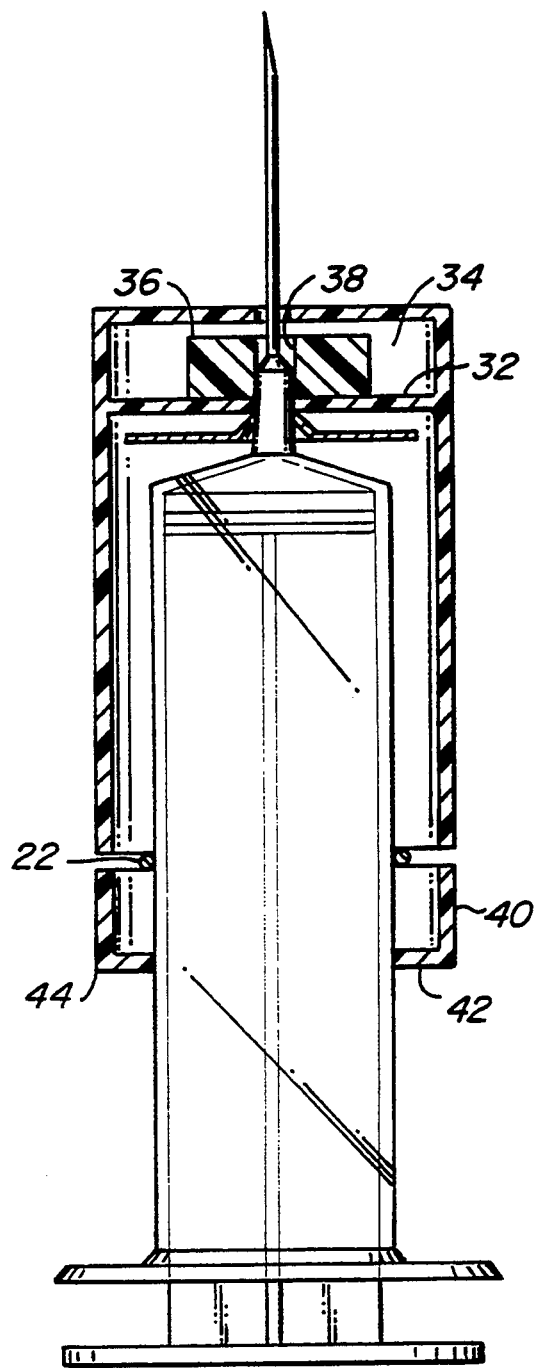

NEEDLE STICK PREVENTION DEVICE

BACKGROUND OF THE INVENTION

The present invention relates to the field of needle stick prevention devices for syringes. After administering an injection, or after withdrawing fluid from a patient, a used syringe presents a safety hazard. Various infectious diseases, such as AIDS and hepatitis B, can be transmitted through the transfer of a small amount of blood from a needle stick. Needle stick prevention devices prevent inadvertent needle sticks from used syringes.

Often, the doctor or nurse does not dispose of the syringe immediately and the syringe lies with the needle unprotected. A passerby or even the person administering the injection can inadvertently contact the needle and receive a needle stick. Even after the syringe is disposed of the needle presents a possible hazard to people who handle the waste containers. If the syringe is disposed of in a conventional trash bag, the needle can pierce the bag and stick the person handling the bag.

A needle stick prevention device is disclosed in U.S. Pat. No. 4,850,994 to Zerbst. A protective cylinder 20 is used to cover the syringe after the injection (FIG. 12 of Zerbst). A back stop 21 engages a catch point 28 which is molded integral with the barrel to prevent the cylinder 20 from moving from the protection position.

A problem with Zerbst is that the cylinder is longer than necessary which adds cost to the device. The catch point 28 of Zerbst is molded in the barrel so that the cylinder 20 not only covers the needle, but part of the barrel as well.

A further problem with Zerbst is that the device cannot be used with a standard syringe. The syringe of Zerbst is specially manufactured with a barrel having the catch point 28 molded into the barrel of the syringe.

SUMMARY OF THE INVENTION

The problems associated with prior art needle stick prevention devices are overcome in accordance with the needle stick prevention device of the present invention. A sleeve is slidably coupled to a syringe between retracted and extended positions. In the retracted, use position the needle is exposed through an aperture in the top of the sleeve. In the extended, protection position the needle is housed within the sleeve thereby preventing inadvertent needle sticks.

The device also includes a mechanism for holding the sleeve in the retracted and extended positions. The holding mechanism prevents the sleeve from interfering with the injection when the sleeve is in the retracted position and prevents the needle from becoming inadvertently exposed when the sleeve is in the extended position. The syringe includes a barrel, a hub having a needle attached thereto, and a shoulder extending between the barrel and hub. An upper stop projects outwardly from the hub of the syringe. When the sleeve is in the extended position the holding mechanism is at least partially positioned between the upper stop and the shoulder thereby holding the sleeve in the extended position.

In a specific, preferred embodiment of the invention, the holding mechanism is a retaining clip having first and second legs. The sleeve preferably has first and second slots in the sidewall which receive the first and second legs, respectively. The legs are positioned against the barrel of the syringe when the sleeve is in the retracted, use position. The legs have a natural, unbiased separation which is smaller than the diameter of the syringe barrel so that the retaining clip applies a modest compressive force on the syringe barrel to hold the sleeve in the retracted position. When the sleeve is moved to the extended, protection position the legs are biased inwardly toward the hub of the syringe between the upper stop and the shoulder. The upper stop is preferably a lock washer which is pressed onto the hub of the syringe.

In another aspect of the invention, the needle stick prevention device includes a sleeve having an intermediate wall positioned between the top and a proximal end of the sleeve. The space between the top and the intermediate wall defines a cavity in which a needle guard is positioned. The needle guard has a hole through which the needle extends when the sleeve is in the retracted position. When the sleeve is in the extended position the needle is housed within the sleeve between the intermediate wall and the proximal end. The needle guard is preferably free to move within the cavity and sized so that in any angular orientation of the sleeve the needle guard obstructs the aperture thereby preventing needle sticks.

The present needle stick prevention device offers the advantage of a smaller size than the needle protection device of Zerbst. The sleeve of the present needle stick prevention device is locked between the shoulder of the syringe and the upper stop thereby providing, in a preferred embodiment, a small, compact sleeve. The cylinder of Zerbst, on the other hand, engages the syringe along the barrel thereby requiring a longer cylinder to cover the needle and part of the barrel as well. An additional advantage of the present needle stick prevention device is that it is adapted to be used with a standard syringe. Some or all of the features of the invention, such as the upper stop, may, of course, be formed integral with a specially manufactured syringe without departing from the scope of the invention.

BRIEF DESCRIPTION OF THE DRAWINGS

FIG. 3 is a cross-sectional view of the needle stick prevention device in an extended position;

FIG. 5 is a cross-sectional view of a needle stick prevention device having a needle guard.

DESCRIPTION OF THE PREFERRED EMBODIMENTS

Figure 1:
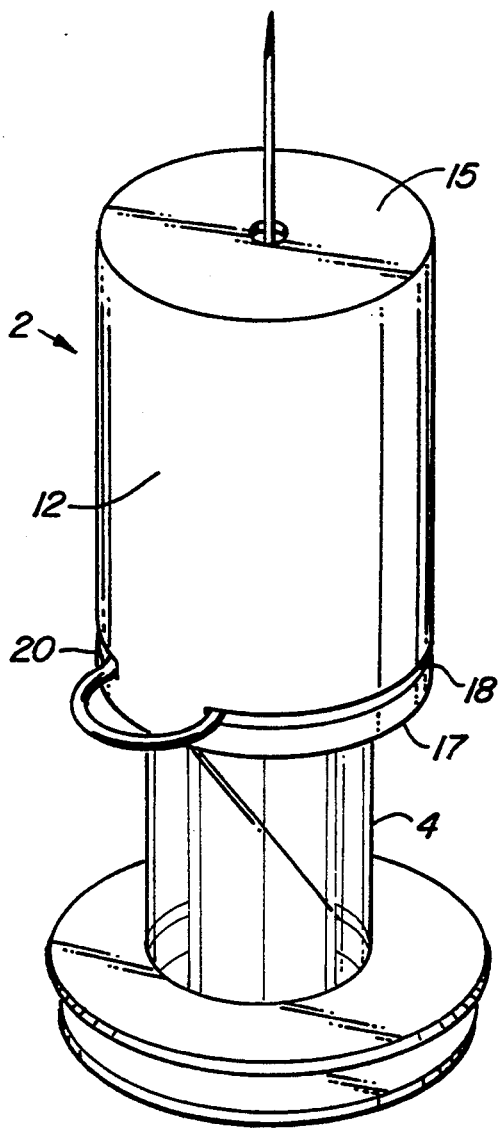
FIG. 1 is an isometric view of a needle stick prevention device in a retracted position.
Figure 2:
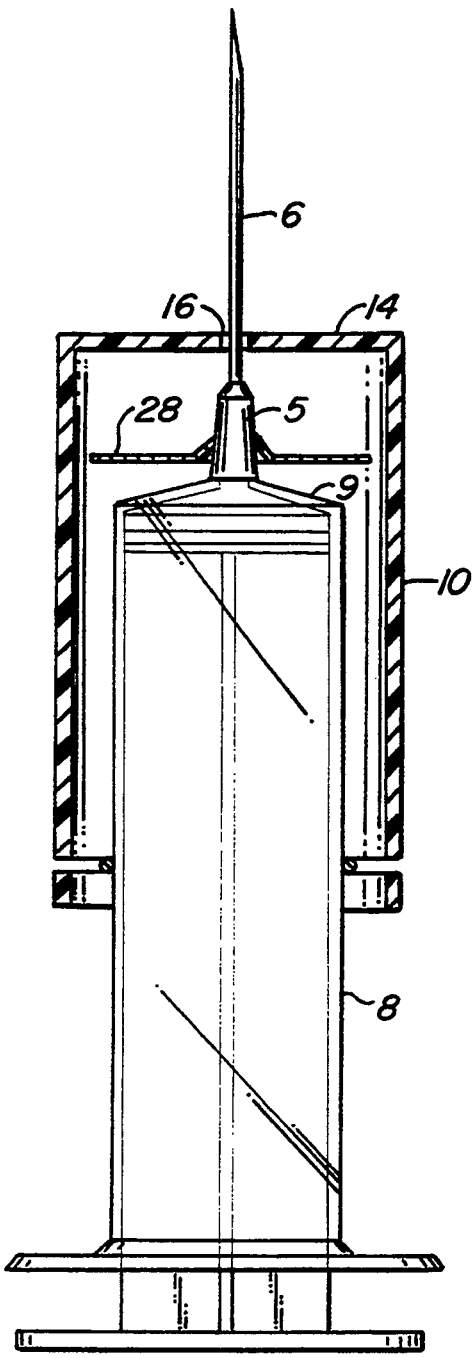
FIG. 2 is a cross-sectional view of the needle stick prevention device of FIG. 1.

A needle stick prevention device 2 for use with a syringe 4 is shown in FIGS. 1 and 2. The syringe 4 includes a hub 5 having a needle 6 attached thereto, a barrel 8, and a plunger. A shoulder 9 extends between the hub 5 and barrel 8. The barrel 8 is preferably cylindrical with an interior wall (unlabeled) and the shoulder 9 is preferably frustoconically shaped. The interior wall has a shape adjacent the shoulder which generally conforms to a shape of the shoulder. As shown in FIGS. 1 and 2, the syringe 4 is preferably a conventional syringe but may also be specially manufactured.

FIG. 1 shows the needle stick prevention device 2 in a retracted position with the needle 6 exposed for use. After the injection, or after withdrawal of fluids from a patient, the device 2 is moved from the retracted position (FIG. 1) to an extended position (FIG. 3). When the device 2 is in the extended position the needle 6 is housed within a sleeve 10 thereby preventing inadvertent needle sticks. The sleeve 10 is held in the retracted and extended positions as described below.

The sleeve 10 includes a sidewall 12 and a top 14 at a distal end 15 (FIGS. 1 and 2). The top 14 has an aperture 16 through which the needle 6 extends when the sleeve 10 is in the retracted position. The sidewall 12 has a length sized so that the needle 6 is recessed below the aperture 16 when the sleeve 10 is in the extended position. The sleeve 10 also includes first and second slots 18, 20 formed near a proximal end 17 of the sleeve. The slots preferably extend perpendicular to a longitudinal axis of the sleeve.

Figure 4:
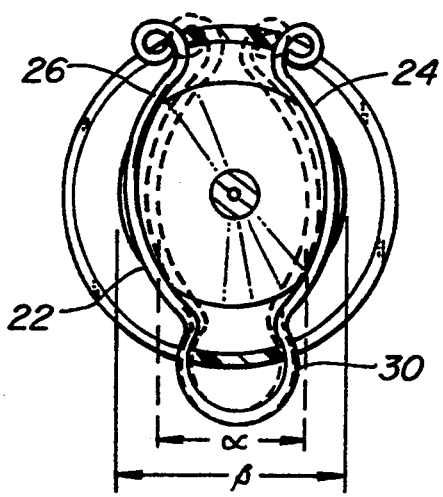
FIG. 4 is a cross-sectional view of the needle stick prevention device of FIG. 3 along line 4—4.

A holding mechanism holds the sleeve in the retracted position so that the sleeve does not interfere with the injection. In a preferred embodiment the holding mechanism is a retaining clip 22 which has first and second legs 24, 26 positioned in the first and second slots 18, 20. The retaining clip 22 has a natural, unbiased shape shown in broken lines in FIG. 4. The legs have a natural, unbiased separation (alpha) which is smaller than a diameter (beta) of the syringe barrel (FIG. 4). Consequently, when the retaining clip is in the retracted position (FIG. 2), the clip applies a modest compressive force to the syringe barrel so that a frictional engagement between the legs 24, 26 and the syringe barrel 8 holds the sleeve 10 in the retracted position.

The holding mechanism also holds the sleeve 10 in the extended position. An upper stop 28 projects outwardly from the hub 5 of the syringe. In the preferred embodiment of FIGS. 1 and 2 the upper stop 28 is a lock washer which is pressed onto the hub 5. When the sleeve 10 is in the extended position the first and second legs 24, 26 of the retaining clip 22 are biased inwardly toward the hub 5 and between the upper stop 28 and the shoulder 9 (FIG. 4). In this manner the sleeve 10 is prevented from moving from the extended protection position of FIG. 3. The retaining clip may take many other forms, for example, the legs may be substantially straight, or the retaining clip may have only one substantially circular leg which cooperates with a single slot circumscribing a substantial part of the barrel circumference.

The retaining clip 22 includes a finger lever 30 for moving the sleeve 10 from the retracted position to the extended position. The retaining clip 22 may also include a pair of finger releases positioned at opposite ends of the legs, rather than a single finger lever. The finger releases may be configured so that when they are pressed together the legs separate thereby making movement of the sleeve 10 from the retracted to extended positions easier.

Figure 6:
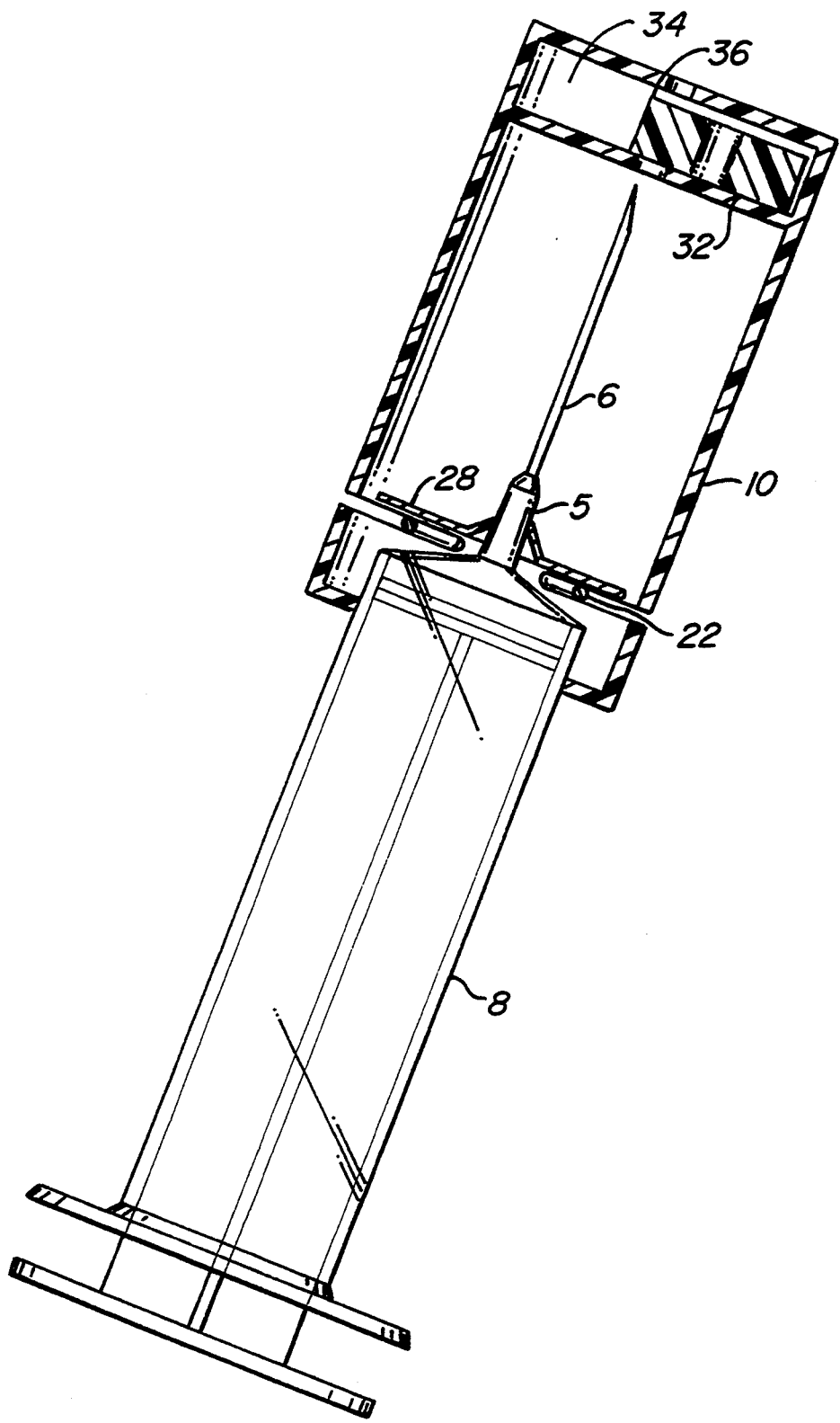
FIG. 6 is a cross-sectional view of the needle stick prevention device of FIG. 5 with the sleeve in the extended position.

A further embodiment of the needle stick prevention device is shown in FIG. 5 in which the sleeve 10 includes an intermediate wall 32. The intermediate wall 32 and the top 14 define a cavity 34 therebetween. A needle guard 36 is housed within the cavity 34 and has a hole 38 through which the needle 6 extends when the sleeve 10 is in the retracted position. After the injection, the sleeve 10 is moved to the extended position of FIG. 6. The needle guard 36 is preferably free to move within the cavity 34 so that the needle guard 36 will slide to a side of the cavity 34. The needle guard 36 is sized to obstruct the aperture 16 in the sleeve 10 in any angular orientation of the sleeve 10 as shown in FIG. 6. The needle guard may be used with any sleeve and syringe configuration and does not necessarily require the holding mechanism described above.

When the needle guard 36 is used with the retaining clip 22 as shown in FIGS. 5 and 6, the needle guard 36 provides additional protection against an inadvertent needle stick. If the retaining clip 22 slides below the syringe shoulder 9 the needle guard 36 will prevent the needle 6 from protruding through the aperture 16. The needle guard 36 is preferably disc shaped but may, of course, take many other forms. In addition, the top 14 or intermediate wall 32, or both, may optionally include a protrusion (not shown) extending into the cavity 34. The protrusion would ensure that the hole 38 and the aperture 16 do not become aligned.

The embodiment illustrated in FIGS. 5 and 6 also includes a sidewall extension 40 which extends below the first and second slots 18, 20. A flange 42 extends radially inward from a bottom 44 of the sidewall extension 40. The flange 42 prevents disengagement of the sleeve 10 from the syringe by limiting movement of the sleeve beyond the extended position. If the first and second legs 24, 26 escape beyond the upper stop 28 toward the needle, the flange 42 will engage the upper stop 28 to prevent the sleeve 10 from becoming completely disengaged from the syringe.

Modification and variation can be made to the disclosed embodiments without departing from the subject of the invention as defined by the following claims. For example, the shoulder could have a catch to engage the first and second legs, the upper stop could be molded integral with the hub, the holding mechanism could be an elastic band or the sleeve, and the shoulder could be flat or rounded rather than frustoconically shaped.

What is claimed is:

1. A needle stick prevention device comprising:
   a syringe including a barrel having an interior wall, a hub having a needle attached thereto, a shoulder extending between the barrel and the hub, a plunger slidably coupled to an interior of the barrel, and a stem attached to the plunger, the interior wall having a shape adjacent the shoulder which generally conforms to a shape of the shoulder, wherein the barrel comprises a cylindrical shape and the shoulder comprises a frustoconical shape;
   an upper stop extending outwardly from the hub;
   a sleeve including a sidewall and a top having an aperture therethrough; and
   means for slidably coupling the sleeve to the syringe between a retracted position, in which the needle extends through the aperture in the top, and an extended position, in which the needle is housed within the sleeve, the slidable coupling means including means for holding the sleeve in the retracted and extended positions, at least a portion of the holding means being biased towards the hub and being at least partially positioned between the upper stop and the shoulder when the sleeve is in the extended position, and the at least portion of the holding means engaging the barrel of the syringe with a compressive force when the sleeve is in the retracted position.

2. The needle stick prevention device of claim 1 wherein:
   the sleeve includes a first slot in the sidewall; and
   the holding means comprises a retaining clip having a first leg positioned in the first slot, the retaining clip being configured to engage the syringe with the compressive force when the sleeve is in the retracted position, the first leg being positioned between the upper stop and the shoulder when the sleeve is in the extended position.

3. The needle stick prevention device of claim 2 wherein:
   the sleeve comprises a second slot;
   the barrel comprises a generally cylindrical shape and a diameter; and
   the retaining clip comprises a second leg positioned in the second slot, the first and second legs having a natural, unbiased separation therebetween smaller than the diameter of the barrel so that when the sleeve is in the retracted position the spring exerts the compressive force on the barrel.

4. The needle stick prevention device of claim 1 wherein the upper stop comprises a lock washer.

5. The needle stick prevention device of claim 1 further comprising:
   an intermediate wall positioned between the top and a proximal end of the sleeve, the top and the intermediate wall defining a cavity therebetween; and
   a needle guard positioned within the cavity and having a hole therethrough, the needle protruding through the hole when the sleeve is in the retracted position.

6. The needle stick prevention device of claim 5 wherein the needle guard is free to move in the cavity under the influence of gravity.

7. A needle stick prevention device comprising:
   a syringe including a barrel, a hub having a needle attached thereto, and a shoulder extending between the barrel and the hub;
   an upper stop extending outwardly from the hub;
   a sleeve including a sidewall, a proximal end, a top having an aperture therethrough, and first and second slots formed in the sidewall, the sleeve being slidably coupled to the syringe between a retracted position, in which the needle extends through the aperture in the top, and an extended position, in which the needle is housed within the sleeve;
   a retaining clip having first and second legs positioned in the first and second slots, respectively, the first and second legs having a natural, unbiased separation, smaller than a diameter of the barrel, the first and second legs being positioned between the upper stop and the shoulder when the sleeve is in the extended position, and the first and second legs being positioned against the barrel when the sleeve is in the retracted position;
   an intermediate wall positioned between the top and the proximal end, the top and the intermediate wall defining a cavity therebetween; and
   a needle guard positioned within the cavity and having a hole therethrough, the needle protruding through the hole when the sleeve is in the retracted position.

8. A needle stick prevention device comprising:
   a syringe including a barrel, a hub having a needle attached thereto, and a shoulder extending between the barrel and the hub;
   an upper stop extending outwardly from the hub;
   a sleeve including a sidewall and a top having an aperture therethrough, the sleeve including a first slot in the sidewall; and
   means for slidably coupling the sleeve to the syringe between a retracted position, in which the needle extends through the aperture in the top, and an extended position, in which the needle is housed within the sleeve, the slidable coupling means including means for holding the sleeve in the retracted and extended positions, the holding means being biased towards the hub and being at least partially positioned between the upper stop and the shoulder when the sleeve is in the extended position, the holding means comprising a retaining clip having a first leg positioned in the first slot, the retaining clip being configured to engage the syringe with a compressive force when the sleeve is in the retracted position, the first leg being positioned between the upper stop and the shoulder when the sleeve is in the extended position.

9. The needle stick prevention device of claim 8 wherein:
   the sleeve comprises a second slot;
   the barrel comprises a generally cylindrical shape and a diameter; and
   the retaining clip comprises a second leg positioned in the second slot, the first and second legs having a natural, unbiased separation therebetween smaller than the diameter of the barrel so that when the sleeve is in the retracted position the spring exerts the compressive force on the barrel.

10. A needle stick prevention device comprising:
    a syringe including a barrel, a hub having a needle attached thereto, and a shoulder extending between the barrel and the hub;
    an upper stop extending outwardly from the hub and comprising a lock washer;
    a sleeve including a sidewall and a top having an aperture therethrough; and
    means for slidably coupling the sleeve to the syringe between a retracted position, in which the needle extends through the aperture in the top, and an extended position, in which the needle is housed within the sleeve, the slidable coupling means including means for holding the sleeve in the retracted and extended positions, the holding means being biased towards the hub and being at least partially positioned between the upper stop and the shoulder when the sleeve is in the extended position.

* * * * *